US00PP18401P3

(12) United States Plant Patent
Zwaan

(10) Patent No.: US PP18,401 P3
(45) Date of Patent: Jan. 8, 2008

(54) ***ACHILLEA* PLANT NAMED 'STRAWBERRY SEDUCTION'**

(50) Latin Name: *Achillea millefolium*
Varietal Denomination: Strawberry Seduction

(75) Inventor: Michiel Zwaan, Alphen aan den-Rijn (NL)

(73) Assignee: K. Sahin, Alphen aan den Rijn (NL)

( * ) Notice: Subject to any disclaimer, the term of this patent is extended or adjusted under 35 U.S.C. 154(b) by 82 days.

(21) Appl. No.: 11/348,957

(22) Filed: Feb. 7, 2006

(65) Prior Publication Data

US 2007/0186322 P1 Aug. 9, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP8,828 P * 7/1994 Bloom ..... Plt./263

OTHER PUBLICATIONS

Anonymous "Technical Guide Tutti Frutti Collection *Achillea* " available at: http://www.yoder.com/grower/perennials/tech_achilleatuttifrutti.pdf year: 2006.*

* cited by examiner

*Primary Examiner*—Wendy Haas
(74) *Attorney, Agent, or Firm*—Penny J. Aguirre

(57) ABSTRACT

A new cultivar of *Achillea millefolium,* 'Strawberry Seduction', characterized by it long blooming habit, its vigorous growth habit, its dense dark green foliage held on sturdy stems, and its red flowers that are consistent in color and resistant to fading.

2 Drawing Sheets

Botanical classification: *Achillea millefolium.*
Variety denomination: 'Strawberry Seduction'.

BACKGROUND OF THE INVENTION

The present invention relates to a new and distinct cultivar of *Achillea* plant, botanically known as *Achillea millefolium* 'Strawberry Seduction' and will be referred to hereinafter by its cultivar name, 'Strawberry Seduction'. The new cultivar of *Achillea* is an herbaceous perennial grown for landscape use.

'Strawberry Seduction' was derived from a breeding program that focused on obtaining *Achillea* cultivars with a long blooming habit and flower colors that are resistant to fading. 'Strawberry Seduction' was selected in the summer of 2001 as a whole plant mutation that arose from repeated selections from seed originally sown of the seed strain *Achillea* 'Summer Pastels' (not patented) in Boskoop, The Netherlands.

'Strawberry Seduction' was selected primarily for its sturdy stems, its uniform red flowers and its thick dark green foliage. 'Summer Pastels', the parent strain, produces plants with variable plant habits and flowers with variable colors and color-fastness. 'Strawberry Seduction' differs from its closest comparison cultivar, *Achillea millefolium* 'Paprika' (not patented), in having sturdier stems, better branching, and shorter stem internodes.

Asexual reproduction of the new cultivar was first accomplished by basal cuttings in under the direction of the inventor in Lancaster, Pa. in September of 2002. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Strawberry Seduction' as unique from all other varieties of *Achillea* known to the inventor.

1. 'Strawberry Seduction' is long blooming, blooming for about five weeks, typically from late July through August in Lancaster, Pa.
2. 'Strawberry Seduction' has red flowers that exhibit minimum fading as they age.
3. 'Strawberry Seduction' is densely foliaged with thick dark green foliage that is held on sturdy stems.
4. 'Strawberry Seduction' has a vigorous growth habit.

BRIEF DESCRIPTION OF THE DRAWING

The accompanying colored photographs illustrate the overall appearance and distinct characteristics of the new *Achillea.*

The photographs shown in FIG. 1. FIG. 1 shows the plant habit in bloom while FIG. 2 is a close-up view of the flowers.

Figure 1:
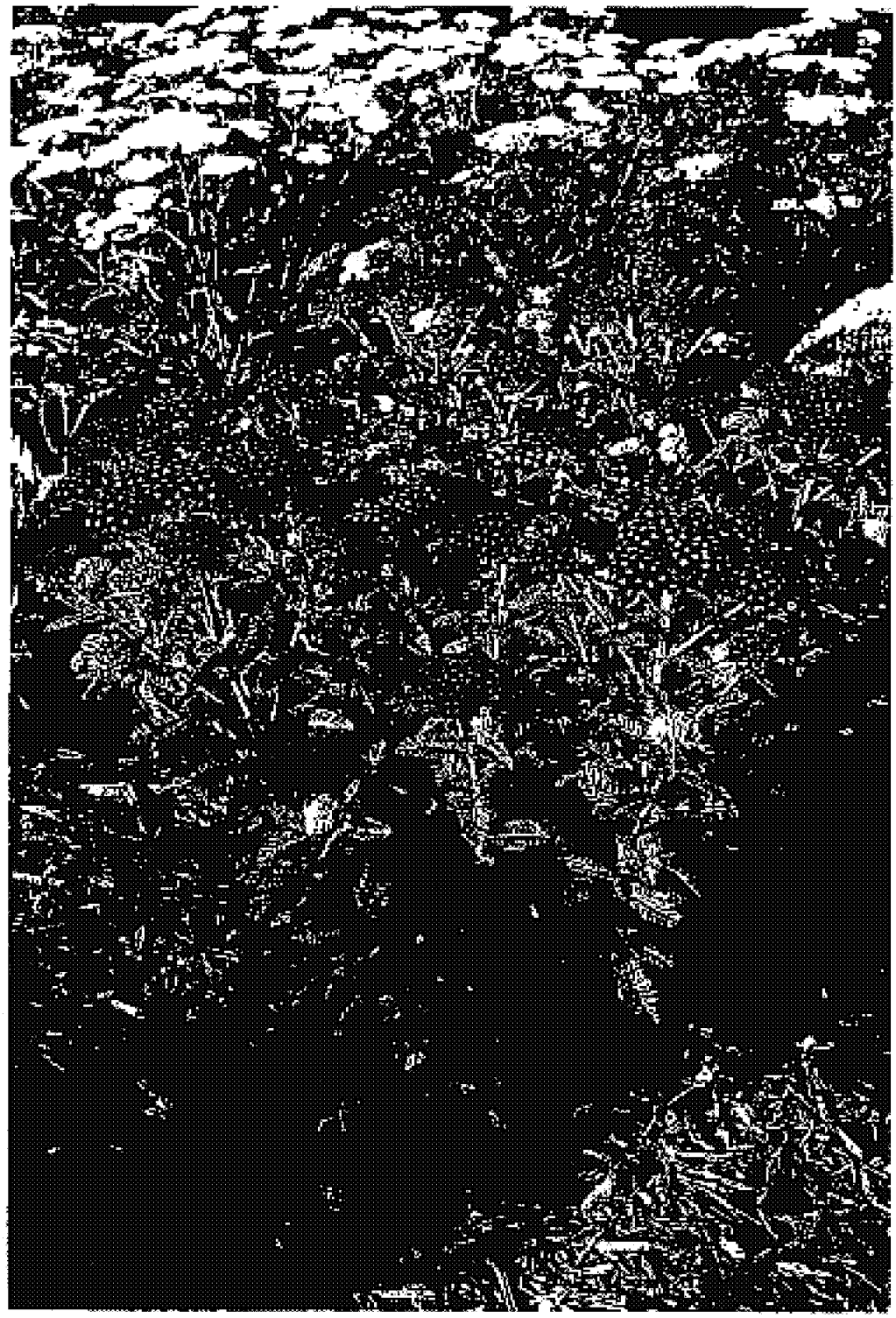
Figure 2:
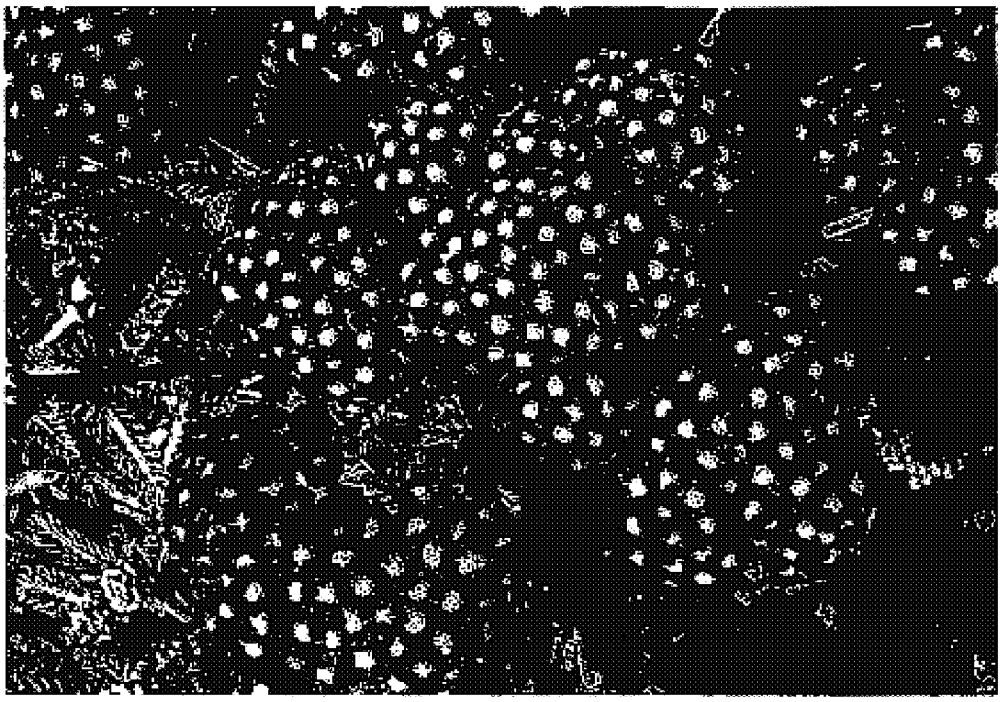
FIG. 2 were taken of two year-old plants as field grown in Lancaster, Pa.
Figure 3:
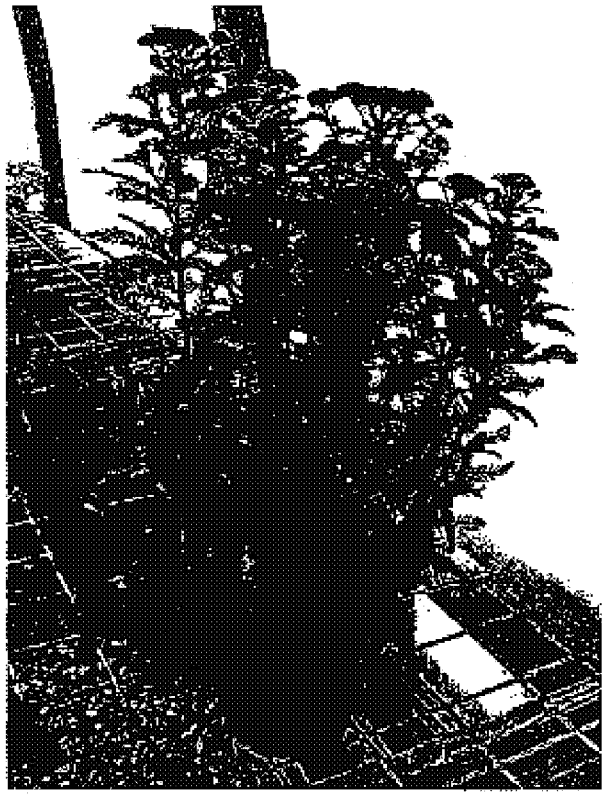

The photograph shown in FIG. 3 was taken in Lancaster, Pa. and depicts a six month-old plant as grown in the greenhouse in a 6-inch container.

The colors in the photographs are as close as possible with the photographic and printing technology utilized. The color values cited in the detailed botanical description accurately describe the colors of the new *Achillea.*

DETAILED BOTANICAL DESCRIPTION

The following is a detailed description of the new cultivar as grown outdoors in for 12 weeks from a liner. The descriptions are based on observations over a period of two years in Lancaster, Pa. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'Strawberry Seduction' is a cultivar of *Achillea millefolium.*

Parentage: Selection from *Achillea millefolium* 'summer Pastels' (seed strain).

General description:

*Blooming period.*—Blooms for about 5 weeks, typically from late July through August in Lancaster, Pa.

*Plant habit.*—Herbaceous perennial, upright, mounded habit, strong flowering stems emerge from a basal rosette of foliage.

*Height and spread.*—Matures to about 46 to 51 cm in height and about 81 cm in width.

*Hardiness.*—U.S.D.A. Zones 4 to 8.

*Culture.*—Tolerant to a wide range of growing conditions, growing best in full sum to in well-drained, moderately fertile soils.

*Diseases and pests.*—No susceptibility or resistance to diseases or pests common to *Achillea millefolium* has been observed for 'Strawberry Seduction'.

*Root description.*—fibrous.

Growth and propagation:

*Propagation.*—Basal stem cuttings.

*Root initiation.*—Basal stem cuttings 8 cm in length dipped in 1000 ppm IBA and placed under mist root in about 10 days in a greenhouse kept at about 70° F. without supplemental lighting in spring and summer.

*Time required for root development.*—Rooted cuttings fully develop a 72-cell in about 4 weeks at 70° F. under mist, cells fully develop and flower in a six inch container in about 12 to 14 weeks when grown outdoors under natural lighting or when grown in a greenhouse at 68° F. without supplemental lighting and a constant liquid feed of 150 ppm N.

*Vernalization.*—Not required, vernalized plant flower about 2 weeks sooner but unvernalized plants had better branching with more flowers.

*Crop maintenance.*—Plants can be cut back after the initial flush of flowers and rebloom occurs in about 4 weeks.

*Growth rate.*—Vigorous.

Stem description:

*Shape.*—Round, solid, sturdy.

*Stem color.*—144B with some blushing of N79B, particularly towards base.

*Stem size.*—Up to 5 mm in diameter, main branches up to 50 cm in length, secondary branches are 10 to 18 cm in length and 2 to 3 mm in diameter.

*Stem surface.*—Glabrous with non-conspicuous fine white hairs and vertical ridges.

*Branching habit.*—Main branches emerge from tuft of basal foliage, typically about 4 to 6 secondary branches emerge from nodes near apex.

*Internode length.*—Average 2 cm.

Foliage description:

*Leaf division.*—Simple, deeply dissected (fern-like).

*Leaf shape.*—Oblanceolate, leaf segments are ovate in outline.

*Leaf base.*—Blunt.

*Leaf apex.*—Acute.

*Leaf margin.*—Finely dissected.

*Leaf venation.*—Only midrib is visible, 144D in color.

*Leaf attachment.*—Sessile, clasping.

*Leaf arrangement.*—Basal foliage in rosettes, opposite on flowering stems.

*Leaf surface.*—glabrous, upper and lower surfaces.

*Leaf color.*—Newly emerged basal foliage; upper and lower surfaces 137C, mature and emerging flowering stem foliage; upper and lower surfaces 137A.

*Leaf size.*—Basal leaves; up to 26 cm in length and 5 cm in width with leaf segments up to 3 cm in length and 2 cm in width, leaves on flowering stems; up to 14 cm (average 10 cm), about 3.5 cm in width with leaf segments about 2 cm in length and 1 cm in width.

*Foliage fragrance.*—Mint-like when crushed.

Flower description:

General description:

*Type.*—Compound corymb composed of numerous, capitulate, heterogamous flowers with ray florets around the head margin and disk florets in the center, forming a radiant head.

*Lastingness of inflorescence.*—About one week until senescence of ray flowers. Bracts and disk flowers are persistent.

*Fragrance.*—None.

*Quantity of inflorescences.*—About 70 flowers on terminal corymb with about 20 to 30 florets on side corymbs, about 300 flowers per flowering stem.

*Corymb size.*—About 6 cm in diameter and 4 cm in depth for terminal corymbs, average of 3.5 cm in diameter and 2 cm in height for side corymbs.

*Flower size.*—About 9 mm in diameter and 6 mm in depth.

*Flower buds.*—About 5 mm in height and 2 mm in diameter, oblong in shape, color 138C with colored apex emerging 8B.

*Peduncle.*—About 0.5 to 1 cm in length and 1.5 mm in diameter, 138B in color, texture is glabrous.

*Pedicel.*—About 4 to 6 mm in length and 1 mm in diameter, 138B in color, texture is glabrous.

*Receptacle.*—Not distinct, small, chaffy, 138C in color.

*Involucral bracts.*—Composed of a series of overlapping bracts, collectively 138D to 138C in color and form a cup (calyx-like) about 3 cm in width and 5 cm in height, individual bracts; about 4 mm in length, 1 mm in width, membranous edges, oblong in shape, acute apex, blunt base.

Ray Florets (pistillate):

*Number.*—5.

*Shape.*—Petal blade is orbicular on narrow tube enclosing pistil.

*Aspect.*—Held flat.

*Size.*—5 mm in length and 3 mm width, showy, blade is 4 mm in length and width, tube portion is 4 mm in length and 0.5 mm in width.

*Petal apex.*—Rounded to blunt with 2 notches (tulip-like).

*Petal base.*—Rounded.

*Petal margins.*—Entire, 2 notches on apex.

*Petal texture.*—Glabrous.

*Color.*—Upper and lower surfaces of petal; tubes portion is 138C throughout development and not visible, showy blade portion emerges yellow 8B with red-purple margins 71A, matures to solid red-purple 71A, fades to solid red-purple 71B.

Disk flowers (bisexual):

*Quantity.*—About 15, densely packed in center of inflorescence.

*Shape.*—Tubular, corolla is fused, flared at apex.

*Size.*—About 5 mm in length and up to 1 mm in width (flare).

*Color.*—Base (tube) is 138D in color, flared portion is translucent with on apex 1B.

Reproductive organs.—

*Presence.*—Disk flowers are perfect, ray flowers are pistillate.

*Gynoecium.*—1 Pistil, bifid stigma, translucent and 1B in color, extends just beyond the flare of disk flowers and emerges at the junction of the tube and showy portion of the petal of the ray flowers. Ovary is 1.5 mm in length, 0.7 mm in width, placement is inferior, translucent in color.

*Androcoecium.*—5 stamens, fused into tube surrounding style, anthers are 1 mm in length and about 0.3 mm in width, translucent, pollen is moderate in abundance and N199B in color.

*Fruit and seed.*—Fruit and seed set has not observed under the conditions tested.

I claim:

1. A new and distinct cultivar of *Achillea* plant named 'Strawberry Seduction' as herein illustrated and described.

* * * * *